US00PP27219P2

(12) United States Plant Patent
Vennik

(10) Patent No.: US PP27,219 P2
(45) Date of Patent: Sep. 27, 2016

(54) ***ZANTEDESCHIA* PLANT NAMED 'ROYAL PUMPKIN'**

(50) Latin Name: ***Zantedeschia* Spreng.**
Varietal Denomination: Royal Pumpkin

(71) Applicant: Jacqueline Vennik, Maarssen (NL)

(72) Inventor: Jacqueline Vennik, Maarssen (NL)

( * ) Notice: Subject to any disclaimer, the term of this patent is extended or adjusted under 35 U.S.C. 154(b) by 103 days.

(21) Appl. No.: 14/544,480

(22) Filed: Jan. 12, 2015

(51) Int. Cl.
*A01H 5/02* (2006.01)

(52) U.S. Cl.
USPC ..... Plt./490

(58) Field of Classification Search
USPC ..... Plt./490
See application file for complete search history.

*Primary Examiner* — Susan McCormick Ewoldt
(74) *Attorney, Agent, or Firm* — Penny J. Aguirre

(57) ABSTRACT

A new cultivar of *Zantedeschia* plant named 'Royal Pumpkin', that is characterized by its flowers that are a blend of orange, red and yellow in color, its high flower yield, its flowers with a long vase life, and its high resistance to *Erwinia caratovora.*

2 Drawing Sheets

Botanical classification: *Zantedeschia* Spreng.
Cultivar designation: 'Royal Pumpkin'.

BACKGROUND OF THE INVENTION

The present invention relates to a new and distinct cultivar of *Zantedeschia* Spreng. and is hereinafter referred to by the cultivar name 'Royal Pumpkin'. 'Royal Pumpkin' represents a new herbaceous perennial grown for use as a potted plant and cut flower.

The new cultivar was derived from a controlled breeding program by the Inventor in Maarssen, The Netherlands. The objective of the breeding program was to develop new cultivars of *Zantedeschia* with high bulb multiplication rates and flowers with high yields, long vase lives, and unique colors. The Inventor made a cross in May of 2006 between the unpatented cultivar 'La Serena' as the female parent and an unnamed and unpatented proprietary plant in the Inventor's breeding program, seedling no. 06213, as the male parent. The Inventor selected 'Royal Pumpkin' in August of 2008 as a single unique plant amongst the seedlings that resulted from the above cross.

Asexual propagation of the new cultivar was first accomplished under the direction of the Inventor by tuber division in 2009 in Breezand, The Netherlands. Asexual propagation by tuber division and tissue culture has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Royal Pumpkin' as a new and unique cultivar of *Zantedeschia.*

1. 'Royal Pumpkin' exhibits flowers that are a blend of orange, red, and yellow in color.
2. 'Royal Pumpkin' exhibits flowers with a long vase life.
3. 'Royal Pumpkin' exhibits high flower yield.
4. 'Royal Pumpkin' has shown a high tolerance to root disease caused by *Erwinia caratovora.*

The female parent of 'Royal Pumpkin', 'La Serena', differs from 'Royal Pumpkin' in having flowers that are more orange-yellow in color and less uniform in color, leaves that are longer, and in having a more vigorous growth habit. The male parent of 'Royal Pumpkin', seedling no. 06213, differs from 'Royal Pumpkin' in having smaller flowers that are deeper orange in color, a more compact plant habit, and smaller leaves. 'Royal Pumpkin' can be most closely compared to the cultivars 'Orania' (2015/0296691), and 'San Remo' (not patented). Orania' is similar to 'Royal Pumpkin' in having flowers in the same color range. 'Orania' differs from 'Royal Pumpkin' in having flowers that are less rounded in shape and more red-orange in color, leaves that are less rounded, and a plant habit that is less upright. 'San Remo' is similar to 'Royal Pumpkin' in having flowers in the same color range. 'San Remo' differs from 'Royal Pumpkin' in having smaller leaves that are more pointed, flowers that are less rounded in shape and more salmon orange in color, and in having a plant habit that is more upright.

BRIEF DESCRIPTION OF THE DRAWINGS

The accompanying colored photographs illustrate the overall appearance and distinct characteristics of the new *Zantedeschia*. The photographs was taken of a plant about 12 weeks in age as grown in a greenhouse in a 6-inch in Honselersdijk, The Netherlands.

The photograph in FIG. 1 provides a side view of 'Royal Pumpkin' in bloom as grown under high light levels.

Figure 1:
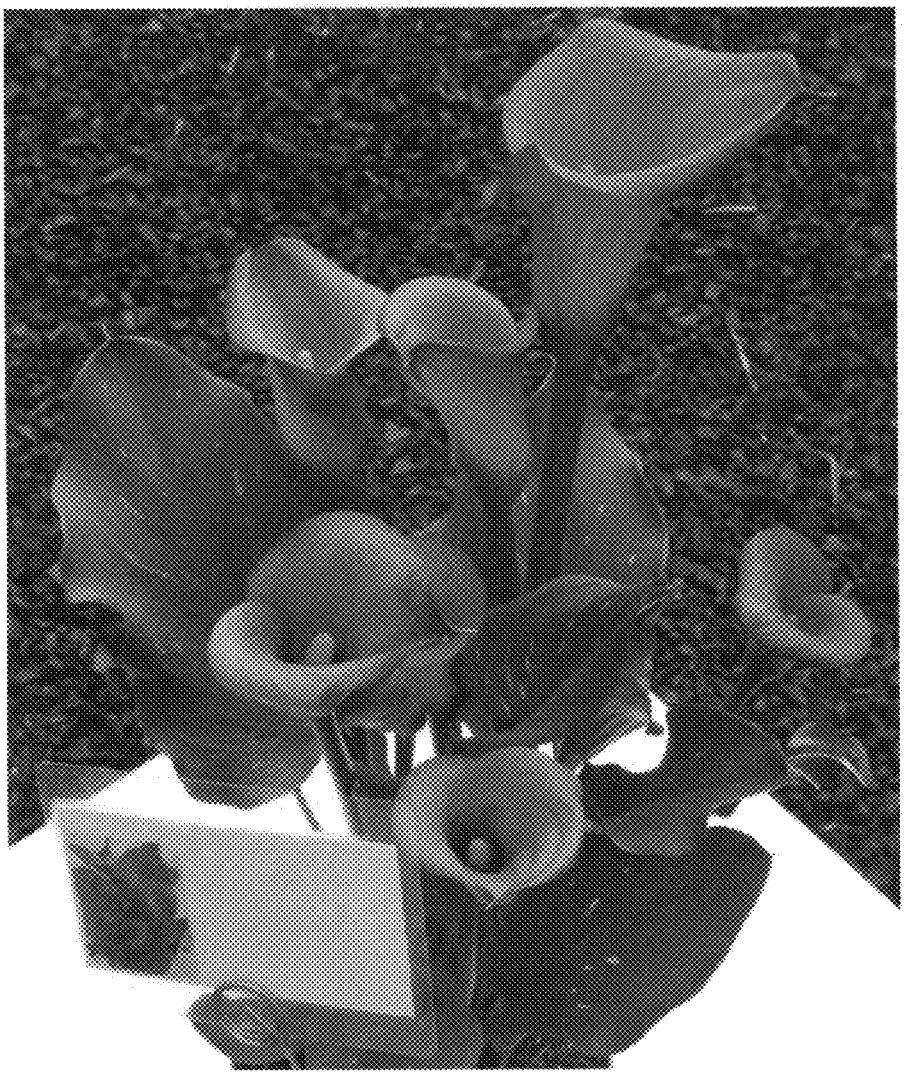
Figure 2:
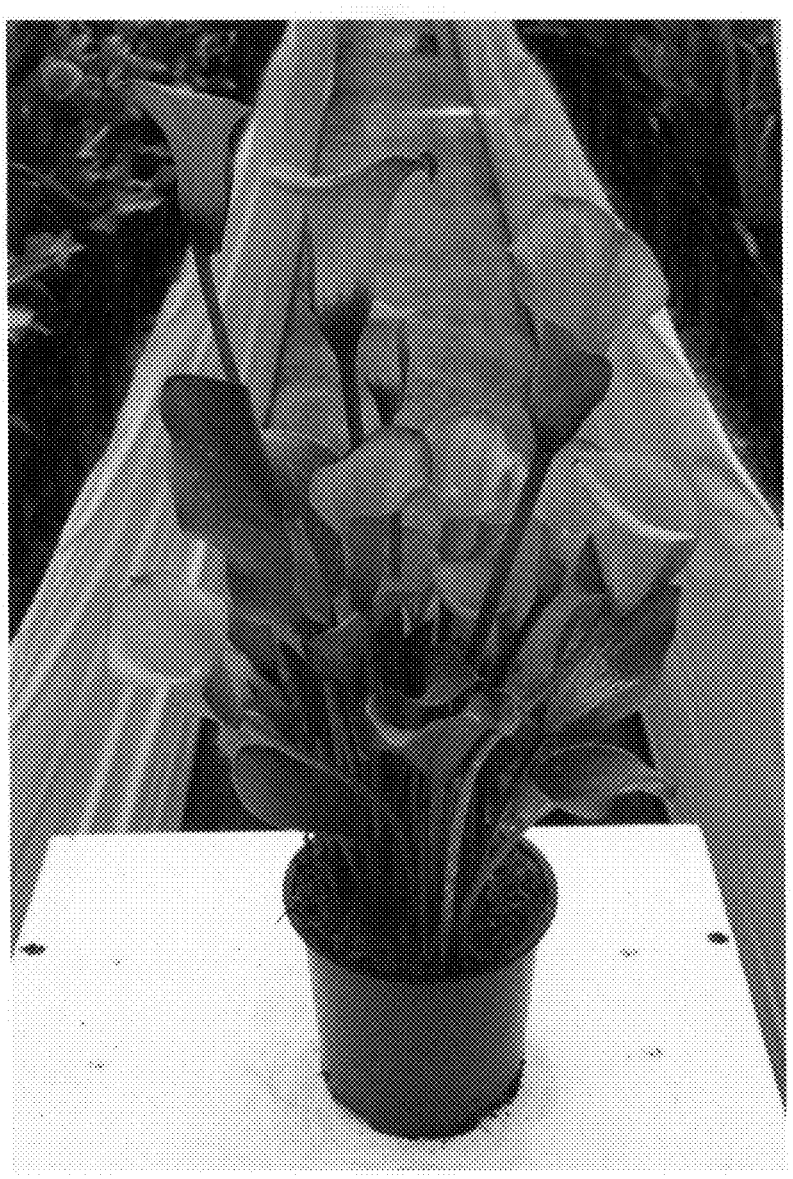

The photograph in FIG. 2 provides a side view of 'Royal Pumpkin' in bloom as grown under low light levels The colors in the photographs may differ slightly from the color values cited in the detailed botanical description, which accurately describe the colors of the new *Zantedeschia.*

DETAILED BOTANICAL DESCRIPTION OF THE PLANT

The following is a detailed description of 12 week-old plants as grown in a greenhouse in 6-inch containers in Honselersdijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—June in Honselersdijk, The Netherlands.

*Plant type.*—Perennial, evergreen with sufficient moisture.

*Plant habit.*—Clump forming, compact, upright with multiple stems.

*Height and spread.*—Average of 45 cm in height to top of inflorescences 30 cm to top of foliage), average of 20 cm in spread as grown in a 6-inch container based on tuber size 18/20 with low levels of plant growth regulator use.

*Hardiness.*—Tropical plant, cold hardy at least in U.S.D.A. Zone 8, good high temperature tolerance.

*Diseases.*—Has shown a high tolerance to *Erwinia caratovora.*

*Root description.*—Thick and fibrous, color about 155A.

*Branching habit.*—Clump forming plant with basal stems, no lateral branches.

*Propagation.*—Tuber division and tissue culture.

*Growth rate.*—Low; produces 8 to 10 harvestable shoots per year and 5 to 7 coarse clumps for division.

*Tuber.*—6 to 8 cm in diameter and 2 to 4 cm in length, 155A in color.

Stem description (peduncle):

*Shape.*—Round with one side flattened.

*Stem color.*—Mature stems; 144B with spots of 144C, young stems; 144D.

*Stem size.*—An average of 30 cm in length and 5 mm in diameter.

*Stem surface.*—Glabrous.

*Stem aspect.*—Held straight upright in an average angle of 0°.

*Stem strength.*—Moderate.

*Stem number.*—An average of 11 per plant as grown in a one-gallon container.

Foliage description:

*Leaf shape.*—Ovate.

*Leaf division.*—Single.

*Leaf base.*—Rounded to slightly cordate.

*Leaf apex.*—Aristate.

*Leaf venation.*—Pinnate, matches leaf color on upper and lower surface.

*Leaf margins.*—Entire and slightly sinuate.

*Leaf attachment.*—Petiolate.

*Leaf arrangement.*—Alternate, growing directly from base.

*Leaf surface.*—Upper and lower surface glabrous and smooth, moderately waxy, and slightly glossy.

*Leaf substance.*—Moderately thick.

*Leaf color.*—Young upper surface; 149D, young lower surface; 144C, mature upper surface; 137A, speckled with small splotches of NN155D with an overlay of 46A, mature lower surface; 137C, speckled with small splotches of NN155D with an overlay of 46A.

*Leaf size.*—An average of 9 cm in length and 5 cm in width.

*Leaf quantity.*—Average of 1 per stem.

Flower description:

*Inflorescence type.*—Spathes with spadices, held above the foliage when fully mature.

*Inflorescence size.*—Up to 8 cm in height and width when fully open.

*Lastingness of inflorescence.*—An average of 3 weeks on plant and 2 weeks as a cut flower, persistent.

*Inflorescence no.*—Continuously produced from new shoots, an average of 13 open at one time as grown in a one-gallon container.

*Inflorescence bud.*—Lanceolate in shape, 6 cm in length and 1.2 cm in width, N144D in color, opens into mature inflorescence shape which increases in size.

*Spathe.*—Broad ovate in shape, strongly cupped with revolute margin, smooth and glabrous on all surfaces, slightly thick and leathery, arrangement; straight on top of peduncle, about 8 cm in length and width and 7 cm across (tube portion about 7 cm in length and 3 cm in width at mid point, apex; mucronate, base; broadly cuneate and wrapped around spadix, color when opening outer surface; 144B and 144C with areas blushed with 182A, color when opening inner surface; a blend of 4C and 150C with narrow margin of 182A and very base 187B, color when maturing outer surface; a blending of 144C in center, 13A at apex and 137D at base with areas suffused with 46A, color when maturing inner surface; 15A and suffused with 46A with very base 187B, color when mature outer surface; a blending of 144B in center, 7A at apex and N77 at base with areas suffused with 183B, color when mature inner surface; 15A and suffused with 46A with very base 187B.

*Spadix.*—Cylindrical in shape tapering towards the top, placed straight on top of the peduncles, apex and base; obtuse, an average of 3.8 cm in length, upper 75% portion contains male flowers and is 5 mm in width and 17B in color, lower 25% contains female flowers and is 1 cm in width and 145D in color.

*Peduncle.*—Described under stem.

*Flower fragrance.*—None detected.

*Flower no.*—Approximately 500 male and 60 female.

*Flower type.*—Male; irregularly oblong in shape (anthers only), an average of 0.7 mm in length and 0.5 mm in width, female; globose in shape, an average of 2.5 mm in diameter.

Reproductive organs:

*Gynoecium.*—Ovaries 145D in color, stigmas 17B in color.

*Androecium.*—Anthers 17B in color, pollen is moderate in quantity and 158A in color.

*Fruit/seed.*—No fruit or seed have been observed.

It is claimed:

1. A new and distinct cultivar of *Zantedeschia* plant named 'Royal Pumpkin' as herein illustrated and described.

* * * * *